United States Patent [19]
Richardson

[11] Patent Number: 5,297,419
[45] Date of Patent: Mar. 29, 1994

[54] LINEARIZING GAS ANALYZER

[75] Inventor: Kent G. Richardson, LaPorte, Ind.

[73] Assignee: Thermco Instrument Corporation, LaPorte, Ind.

[21] Appl. No.: 914,553

[22] Filed: Jul. 16, 1992

[51] Int. Cl.$^5$ ............................................. G01N 31/00
[52] U.S. Cl. ..................... 73/25.03; 73/25.01; 422/83; 422/96; 422/98; 422/90
[58] Field of Search ................. 422/83, 98, 90, 96; 73/25.03, 25.01

[56] References Cited

U.S. PATENT DOCUMENTS

| | | | |
|---|---|---|---|
| 3,429,178 | 2/1969 | Durbin | 73/25.03 |
| 3,480,397 | 11/1969 | Baumgartel | 73/25.03 |
| 3,533,858 | 10/1970 | Seibel et al. | 73/25.03 |
| 3,756,069 | 9/1973 | Carswell, Jr. et al. | 73/25.03 |
| 3,786,675 | 1/1974 | Delatorre et al. | 73/25.03 |
| 3,943,751 | 3/1976 | Akiyama et al. | 73/25.03 |
| 4,164,862 | 8/1979 | Jackson | 73/25.03 |
| 4,519,237 | 5/1985 | Kubo | 73/25.03 |
| 4,541,988 | 9/1985 | Tozier et al. | 73/25.03 |
| 4,944,035 | 7/1990 | Roger L. et al. | 73/25.03 |
| 4,970,891 | 11/1990 | Blevins et al. | 73/25.03 |

Primary Examiner—Robert J. Warden
Assistant Examiner—Hien Tran
Attorney, Agent, or Firm—James D. Hall; Thomas J. Dodd

[57] ABSTRACT

A machine for analyzing and displaying the concentration of a pressurized gas flowing through a delivery line in relationship to a reference gas. The machine includes a thermal conductivity detector which is connected to a microprocessor and a visual display. The microprocessor allows the machine operator to select any of a number of references and sample gas combinations for analysis.

7 Claims, 2 Drawing Sheets

LINEARIZING GAS ANALYZER

FIELD OF THE INVENTION

This invention relates to gas analyzers and will have special application to analyzers which display the value of a sample gas in relation to a second, or reference gas.

BACKGROUND OF THE INVENTION

Gas analyzers are useful machines for measuring the content of gas mixtures, particularly, the gas industry and in industrial uses of various gas mixtures. Previous gas analyzers include those which utilize infrared radiation, chemical cells, and thermal conductivity sensors. The content of a given gas can be computed by comparing its known properties against the readout displayed by the analyzer.

Prior art gas analyzers required frequent calibration and could not be readily adapted to measure varying mixtures of sample and reference gases. Particularly, analyzers which measured content based on thermal conductivity required that the user change the analyzer current, mix a number of known samples to determine the analyzer output at each mixture, calculate the analysis curve and enter the data, and finally to recalibrate the gas range with a known accurate gas sample. This procedure sometimes takes a full working day for an instrument technician to accomplish. Often, the prior machines were returned to the factory for recalibration at the customer's expense.

SUMMARY OF THE INVENTION

The gas analyzer of this invention combines microprocessor technology with the gas analyzer to allow for a rapid determination of gas content in a variety of gases of large ranges. This determination can be made by simply depressing a switch of the analyzer to change the linearization curve generated by the sensors and analyzed by the microprocessor. The value of the sample gas is visually displayed on a screen by a light emitting diode.

Accordingly, it is an object of this invention to provide for a gas analyzer which is capable of analyzing any of a number of sample gases at various concentrations relative to a reference gas.

Another object is to provide a gas analyzer which is readily adaptable for analysis of a mixture of various sample gases in a variety of reference gases.

Another object is to provide for a gas analyzer which can be custom tuned to analyze any combination of gases quickly and easily.

Other objects will become apparent upon a reading of the following description.

BRIEF DESCRIPTION OF THE DRAWINGS

A preferred embodiment of the invention has been depicted for illustrative purposes only wherein.

DESCRIPTION OF THE PREFERRED EMBODIMENT

Figure 1:
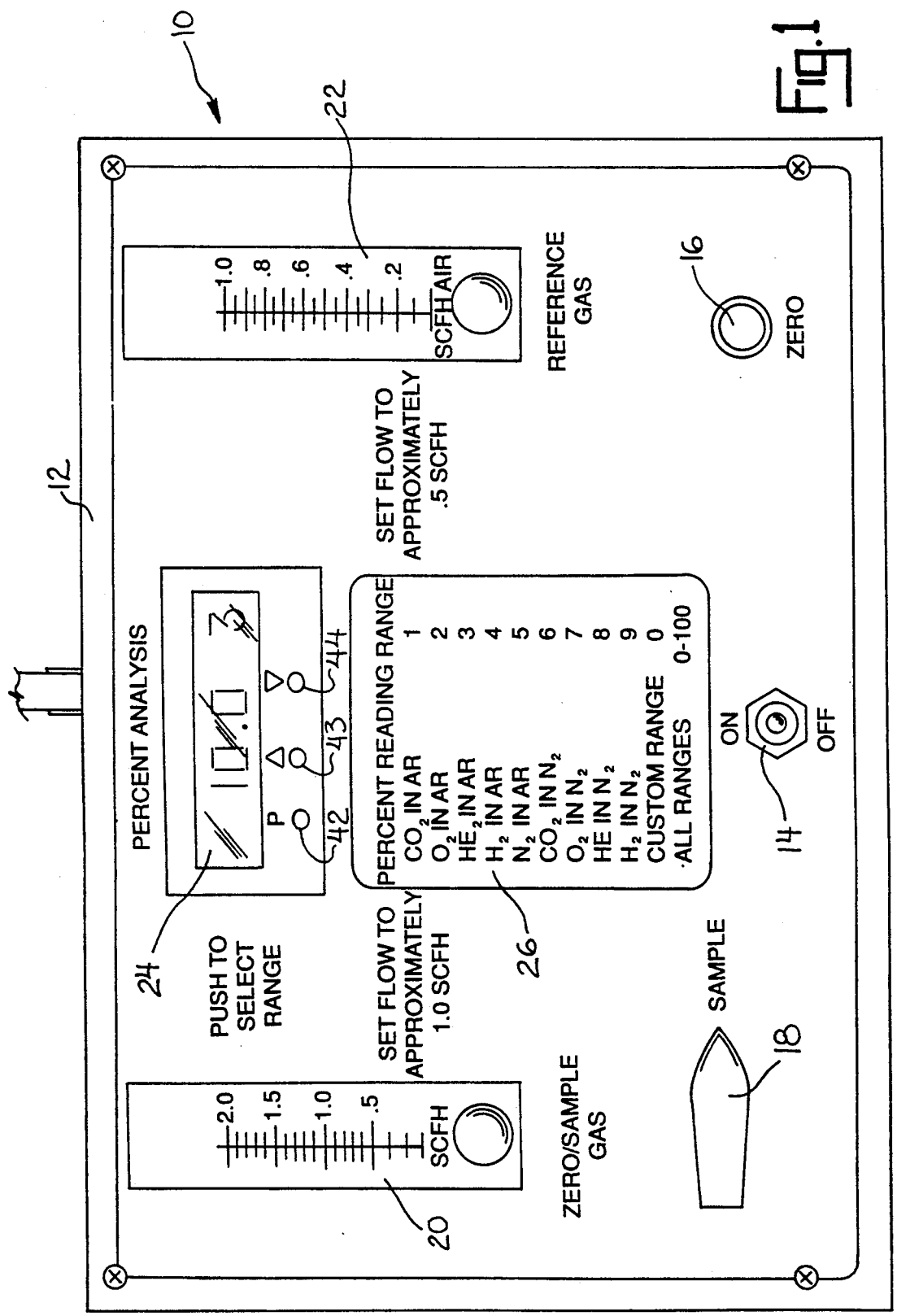
FIG. 1 is a plan view of the front panel of the gas analyzer of this invention.

The preferred embodiment herein described is not intended to be exhaustive or to limit the invention to the precise form disclosed. It is chosen and described to explain the principles of the invention and its application and practical use to enable those skilled in the art to follow its teachings.

Referring to the drawings, reference numeral 10 generally designates the gas analyzer of this invention. Analyzer 10 is used to detect the passage of one or more gases and to display the concentration of a sample gas which is mixed with a reference gas.

FIG. 1 illustrates in plan view, the front panel 12 of analyzer 10. Front panel 12 carries various functional parts namely power switch 14, zero adjustment knob 16, selector switch 18, flow meters 20 and 22, and visual display panel 24. Table 26 is imprinted on front panel 12 to allow the analyzer operator a quick reference as to the gas mixture ranges which can be tested.

Gas analyzer 10 operates under the known principle of thermal conductivity. That is, each gas to be tested will conduct heat at a specific rate. By flowing the gases across a device which measures this conductivity, and comparing the values to known values for each gas, the concentration of each gas can be determined.

Figures 2, 3:
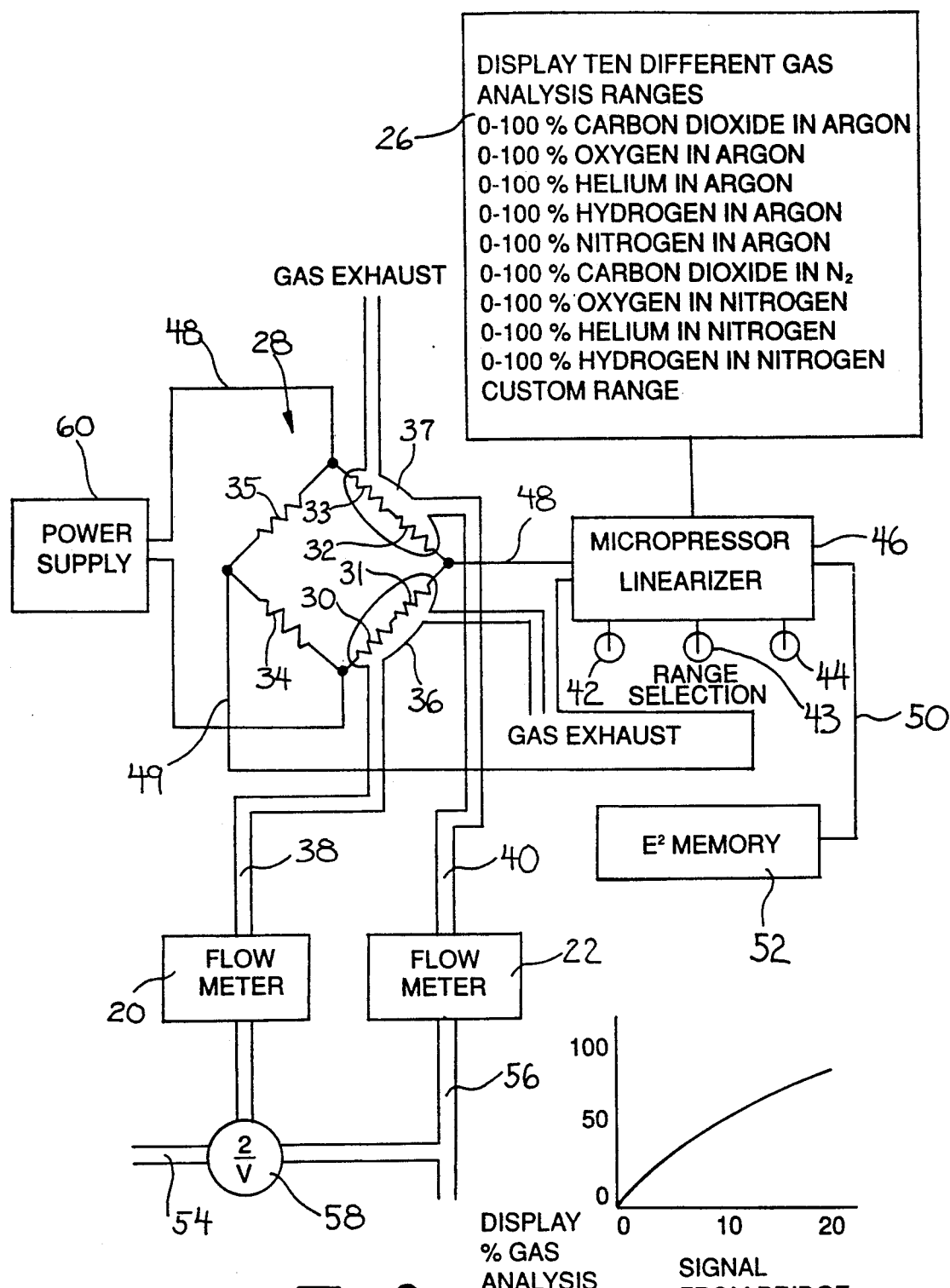
FIG. 2 is a schematical view of the gas analyzer.
FIG. 3 is a graphical representation of a typical gas mixture analytical curve.

FIG. 2 illustrates in schematic form the internal components of analyzer 10 which perform the thermal conductivity measurements. The main component of the analyzer 10 which performs the conductivity measurement is the Wheatstone Bridge 28 which is of a closed loop configuration and includes metal filaments 30, 31, 32, 33 connecting fixed value resistors 34, 35.

Sample gases to be tested under analyzer 10 through inlet lines 38, 40. After adjusting the flow of the gases by visual inspection of flow meters 20, 22, the operator selects the desired range by manipulating buttons 42, 43, 44 on the front panel 12. As shown in FIG. 3, the flow rates should be adjusted to 1.0 standard cubic feet per hour (SCFH) and 0.5 SCFH for the sample and reference gases, respectively, to obtain an accurate reading.

The well-known principle of thermal conductivity states that each gas will conduct heat at a different rate. As the gases flow into the gas chambers 36, 37 of the Wheatstone Bridge 28 the gas mixtures carry heat away from the filaments 30–33 which change is indicated by the bridge including the balance resistors 34–35. The electrical signal changes as the heat dissipates and is transmitted to microprocessor/linearizer 46 by lead lines 48, 49. The microprocessor/linearizer 46 is connected as by lead 50 to memory chip 52 which stores the various range equivalents and their conversion factors.

Unfortunately, the rate at which heat is dissipated by most binary gas mixtures generates a non-linear curve (see FIG. 3). Microprocessor/linearizer 46 selects the appropriate curve to be used in response to signals from buttons 42–44, and sends the results to display panel 24 where the operator may visually observe the gas concentrations.

Analyzer 10 may be used to analyze mixtures of two gases, comparing a sample gas to a reference gas. The reference gas is usually 100% Argon or Nitrogen or other inert gas as seen in range table 26. The sample gas may consist of carbon dioxide, oxygen, helium, hydrogen, nitrogen and others.

Analyzer 10 is designed to analyze the nine different gas mixtures displayed on the table 26 in any range. Also, the operator may elect to program a tenth gas mixture analytical curve into microprocessor memory 52 in a conventional manner.

Analyzer 10 is operated as follows. Sample and reference gas sources (not shown) are connected to inlet ports 54, 56 respectively. Additionally, two way valve 58 is set to allow only the reference gas to pass through into inlet lines 38, 40. Power switch 14 is flipped on and power supply 60 sends electric current through filaments 30–33 to heat the filaments to a predetermined temperature.

After a suitable warm-up time, the reference gas is flowed through lines 38, 40 and across Wheatstone Bridge 28 to obtain a zero reading. Valve 58 is then switched to allow only the sample gas to pass into inlet line 38 with the reference gas passing through line 40. Since the sample gas is generally a mixture of the reference gas and a second gas, heat from the filaments 30, 31 will be dispersed at a different rate than from filaments 32, 33. The heat dissipation rate is sensed by the bridge 34–37 and signals are sent via leads 48, 49 to microprocessor 46. Depending upon the input from memory 52, microprocessor 46 linearizes the differing signals and sends a command to visual display 24 which accurately shows the concentration of the sample gas. The following examples are indicative of the operation of analyzer 10.

EXAMPLE 1

Analyzer 10 is configured to analyze a sample gas of Helium in combination with an Argon reference gas. The operator selects range 3 on the table 26 by manipulating buttons 42–44 until the number "3" appears on the right side of display 24.

Pure argon gas is then flowed through lines 38, 40 across Wheatstone Bridge 28. The pure reference gas passing over bridge 28 produces an output signal of 0 MV which is related to microprocessor/linearizer 46. The value is compared with the % reading received from memory 52 and determined to be 0. This value is relayed to display 24 which displays the numeral 0 on the panel.

The operator then introduces the sample gas into line 38 by switching value 58 to the "sample" setting. The gas sample theoretically contains 10% helium in argon. As this sample gas passes across filaments 30, 31 it conducts heat from those filaments and carries off the heat at a different rate than the heat carried off from filaments 32, 33 over which 100% argon flows. This difference is 306.1 MV and is relayed to microprocessor/linearizer 46 which converts the value to 10.0% He, and this value is displayed on screen 24 as shown in FIG. 1. The following table illustrates the MV values sent to microprocessor/linearizer 46 for differing concentrations of He in Ar.

| POINT | RANGE 3 0–100.0% Helium in Argon MV TO METER | % READING |
|---|---|---|
| ZERO | 0 | 0 |
| 1 | 88.65 | 2.5 |
| 2 | 168.8 | 5.0 |
| 3 | 241.4 | 7.5 |
| 4 | 306.1 | 10.0 |
| 5 | 376.1 | 13.0 |
| 6 | 438.6 | 16.0 |
| 7 | 494.6 | 19.0 |
| 8 | 545.0 | 22.0 |
| 9 | 590.6 | 25.0 |
| 10 | 632.1 | 28.0 |
| 11 | 670.0 | 31.0 |
| 12 | 704.7 | 34.0 |
| 13 | 736.7 | 37.0 |
| 14 | 766.2 | 40.0 |
| 15 | 793.5 | 43.0 |
| 16 | 818.9 | 46.0 |
| 17 | 842.5 | 49.0 |
| 18 | 864.4 | 52.0 |
| 19 | 884.9 | 55.0 |
| 20 | 904.1 | 58.0 |
| 21 | 922.0 | 61.0 |
| 22 | 938.9 | 64.0 |
| 23 | 954.8 | 67.0 |
| 24 | 969.8 | 70.0 |
| 25 | 984.1 | 73.0 |
| 26 | 997.7 | 76.0 |
| 27 | 1010.6 | 79.0 |
| 28 | 1023.1 | 82.0 |
| 29 | 1035.0 | 85.0 |
| 30 | 1046.3 | 88.0 |
| 31 | 1057.1 | 91.0 |
| 32 | 1067.1 | 94.0 |
| 33 | 1076.2 | 97.0 |
| 34 | 1084.0 | 100.0 |

EXAMPLE 2

The same procedures are followed as in Example 1 except the sample gas contains a hydrogen-argon mixture. The following table for range 4 illustrates the non-linear curve generated by differing H concentrations and comparable MV-% readings which appear on screen 24.

| POINT | RANGE 4 0–100.0% Hydrogen in Argon MV TO METER | % READING |
|---|---|---|
| Zero | 0 | 0 |
| 1 | 139.8 | 2.5 |
| 2 | 255.0 | 5.0 |
| 3 | 350.4 | 7.5 |
| 4 | 430.6 | 10.0 |
| 5 | 511.4 | 13.0 |
| 6 | 579.1 | 16.0 |
| 7 | 636.8 | 19.0 |
| 8 | 686.7 | 22.0 |
| 9 | 730.0 | 25.0 |
| 10 | 767.9 | 28.0 |
| 11 | 801.2 | 31.0 |
| 12 | 830.5 | 34.0 |
| 13 | 856.2 | 37.0 |
| 14 | 879.1 | 40.0 |
| 15 | 899.5 | 43.0 |
| 16 | 918.1 | 46.0 |
| 17 | 935.3 | 49.0 |
| 18 | 953.0 | 52.0 |
| 19 | 969.0 | 55.0 |
| 20 | 983.5 | 58.0 |
| 21 | 996.5 | 61.0 |
| 22 | 1008.0 | 64.0 |
| 23 | 1019.0 | 67.0 |
| 24 | 1029.0 | 70.0 |
| 25 | 1039.0 | 73.0 |
| 26 | 1049.0 | 76.0 |
| 27 | 1057.0 | 79.0 |
| 28 | 1060.0 | 82.0 |
| 29 | 1073.0 | 85.0 |
| 30 | 1080.0 | 88.0 |
| 31 | 1086.0 | 91.0 |
| 32 | 1092.0 | 94.0 |
| 33 | 1097.0 | 97.0 |
| 34 | 1106.0 | 100.0 |

Other precalculated ranges for other gas mixtures are well-known and are preentered so that analyzer 10 can quickly and accurately analyze the desired gas mixture to ensure the quality of the gas source.

The invention described is not limited to the given details, but may be modified within the scope of the following claims.

I claim:

1. A machine for analysis of gas mixtures, said machine comprising a housing, first inlet means for introducing a first gas sample into said housing, second inlet means for introducing a second gas sample into said housing, means positioned across said first and second inlet means for detecting thermal conductivity of the first gas sample relative to the second gas sample, means for comparing a difference between thermal conductivities of the first gas sample and the second gas sample, memory means connected to said means for comparing, said memory means for converting the difference in thermal conductivity into a first gas percentage reading, means for visually displaying the percentage reading connected to said means for comparing, said memory means housing a plurality of different thermal conductivity ranges based upon different compositions of the first and second gas samples.

2. The machine of claim 1 wherein said means for detecting thermal conductivity includes a Wheatstone bridge.

3. The machine of claim 1 wherein said memory means includes stored data for a multiplicity of gas thermal conductivity curves, and said machine includes switching means connected to said memory means for selecting an appropriate one of said gas thermal conductivity curves based upon different compositions of a fast gas and second gas samples.

4. The machine of claim 3 wherein said switching means includes a selector button accessible from an exterior of the machine.

5. The machine of claim 3 and further comprising a printed table carried by said machine, said table constituting means for identifying a plurality of different gas mixtures being analyzed.

6. A machine for analyzing a sample gas concentration in a sample gas-reference gas mixture wherein the sample gas and reference gas have dissimilar and known thermal conductivity curves, said machine comprising a housing, first inlet means for introducing a reference gas into said housing, second inlet means for introducing a mixture of said reference gas and a sample gas into said housing, means positioned across said first and second inlet means for detecting thermal conductivity of the reference gas relative to the sample gas-reference gas mixture, means for comparing a difference between thermal conductivities of the reference gas and the reference gas-sample gas mixture, memory means for converting the difference in thermal conductivity into a sample gas percentage reading, said memory means housing a plurality of different thermal conductivity ranges for different reference gas-sample gas mixtures, and means for visually displaying concentration of the sample gas in the reference gas-sample gas mixture.

7. A machine of claim 6 wherein said memory means includes stored data for a multiplicity of gas thermal conductivity curves, and said machine includes switching means connected to said memory means for selecting an appropriate one of said gas thermal conductivity curves based upon the different reference gas-sample gas mixtures.

* * * * *